Figure 4:
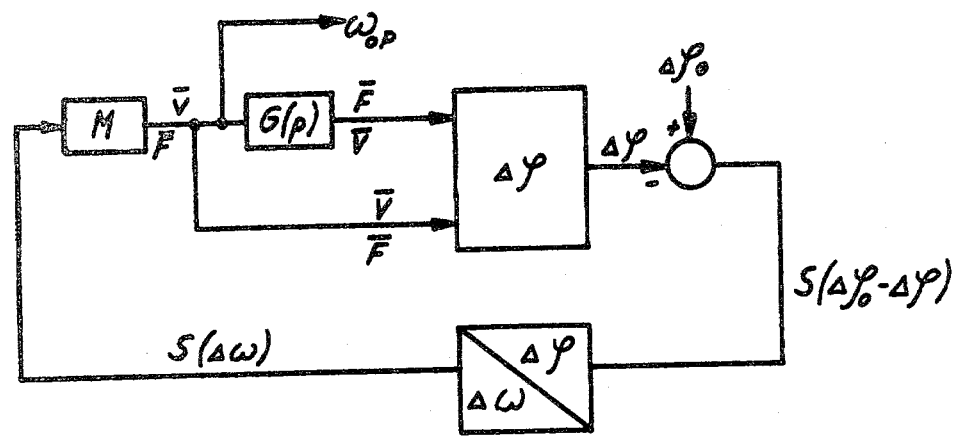

United States Patent [19]

Leupp

[11] 4,307,610
[45] Dec. 29, 1981

[54] METHOD FOR MEASURING CRACK PROPAGATION IN SAMPLES, AND A HIGH FREQUENCY PULSATOR FOR CARRYING OUT THE METHOD

[75] Inventor: Jürg Leupp, Feuerthalen, Switzerland

[73] Assignee: Swiss Aluminium Ltd., Chippis, Switzerland

[21] Appl. No.: 51,216

[22] Filed: Jun. 22, 1979

[30] Foreign Application Priority Data

Jun. 26, 1978 [CH] Switzerland .................. 6911/78

[51] Int. Cl.³ .................. G01H 13/00; G01N 3/32
[52] U.S. Cl. .................. 73/579; 73/799
[58] Field of Search .................. 73/579, 574, 577, 578, 73/799, 808, 811

[56] References Cited

U.S. PATENT DOCUMENTS

| | | | |
|---|---|---|---|
| 3,622,404 | 11/1971 | Thompson | 73/579 |
| 4,003,246 | 1/1977 | Cain | 73/799 |
| 4,026,142 | 5/1977 | Jacobs | 73/578 |
| 4,128,011 | 12/1978 | Savage | 73/579 |

FOREIGN PATENT DOCUMENTS 1904864 9/1969 Fed. Rep. of Germany .

Primary Examiner—Stephen A. Kreitman
Attorney, Agent, or Firm—Bachman and LaPointe

[57] ABSTRACT

A method for measuring crack propagation in samples as a function of the number of load cycles is proposed wherein changes in the frequency response of a mechanical impedance of a sample which is to be tested is registered. At a pulsation frequency, which corresponds to the resonant frequency of the sample, there is a rise in the resonance of the mechanical impedance, defined as the quotient of the speed of movement of the sample and the applied pulsating force. Since, when a crack grows in the sample, its elastic constant decreases along with the cross-sectional area, the frequency response of the sample shifts towards lower frequences. To carry out the process of the invention it is suggested that the phase of the above mentioned impedance or an impedance which is dependent on it should be detected, or else to register the impedance magnitude whilst keeping the force acting on the sample or the speed of movement constant, or else to register the force or speed of movement as a function of the number of load cycles and standardized with respect to the appropriate values of momentary load or speed of movement.

16 Claims, 13 Drawing Figures

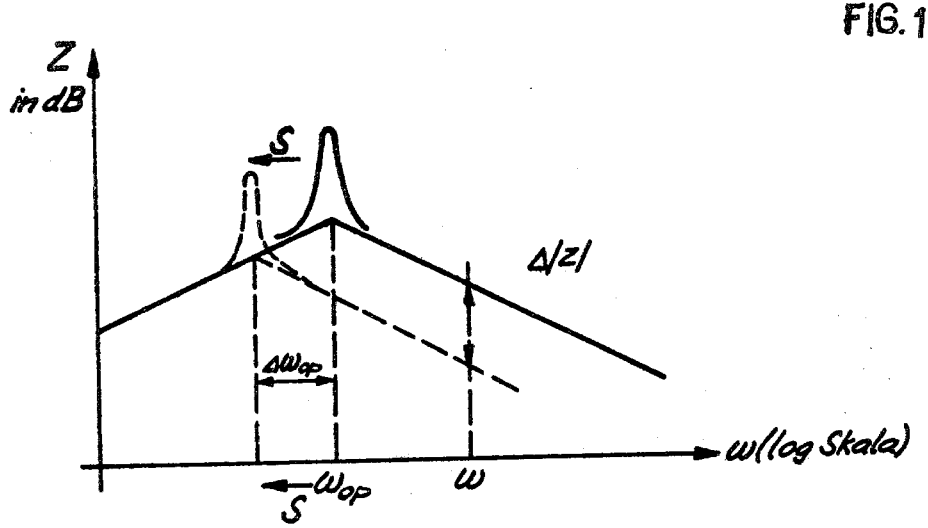
FIG. 1
FIG. 1a
FIG. 1b
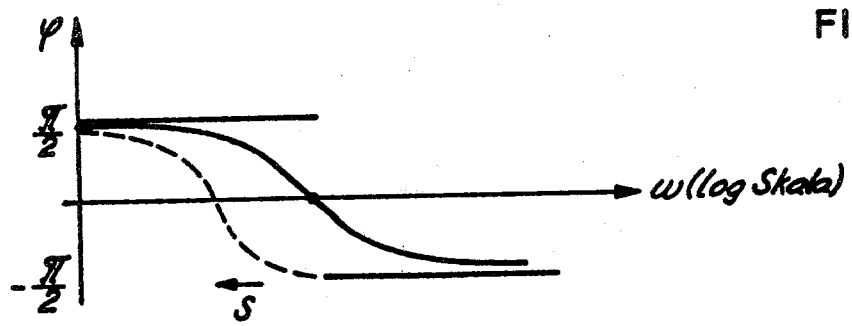
FIG. 2
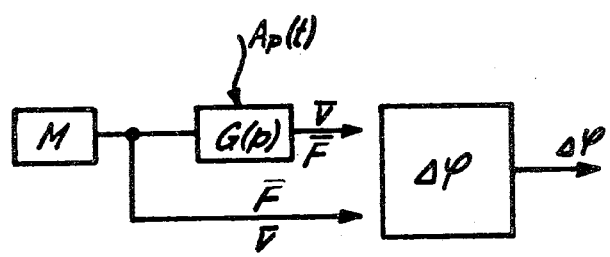
FIG. 3

METHOD FOR MEASURING CRACK PROPAGATION IN SAMPLES, AND A HIGH FREQUENCY PULSATOR FOR CARRYING OUT THE METHOD

The invention concerns a method for measuring crack propagation in samples subjected to cyclic loading, and concerns too a high frequency pulsator for carrying out the method.

In modern fracture mechanics the value da/dN (crank propagation per load cycle) has become indispensible as a characteristic value for assessing the fatigue behavior of a material or a component.

As a result, pulsators or electro-magnetic resonance machines e.g. from "Instron Ltd." which allow the samples to be subjected to more or less sinusoidal cyclic loading have been developed, with crack propagation being followed at the surface with the help of an optical microscope. Depending on the conditions of the test, a decision is made from a certain specified crack length is reached, and the course of the test altered by the operator. This method requires continuous observation of the crack and therefore the almost continuous presence of the operator throughout the test. Consequently tests cannot be run overnight or at weekends. The equipment is therefore not well utilized and the test must be relatively brief. The behavior of the crack at the surface may not correspond at all with the behavior inside the sample. Also, the supervision of the sample requires experienced personnel.

Other, known methods of measurement make use of devices fitted to the sample, for example foils e.g. from "Rumul" strain gauges to measure crack opening displacement e.g. from "Kyowa" or "Instron", or eddy current devices.

The purpose of the invention is as follows:

A fully automatic method of measurement is proposed, by means of which, and without incurring difficulty, once a crack has occurred or is provided in a probe, the propagation of the crack can be detected and converted into electrical signals, which, depending on the conditions of the test, allow feed back control of the pulsator and automatic registration of the progress of the crack on conventional recording facilities such as chart recorders, punched tape, tape or disc-storage facilities etc. The effective change in cross-sectional area of the sample perpendicular to the direction of loading should be recorded so that any secondary cracks which might appear at the edges or inside the sample can be taken into account. As specimen or probe with well-defined crack fracture mechanic specimens or probes are preferably used which are notched per definitionem.

The proposed method of the invention as described in claim 1 achieves this aim.

If one takes into account, however, that the change in the amplitude-frequency characteristic of a body capable of resonating depends not only on a shift in resonant frequency but also on any dampening which may occur, then the method as described in claim 3 is required for high precision measurement.

The version of the method described in claim 4 allows particularly good resolution in the measurement of crack propagation.

If it is desirable to work at relatively high loading frequencies, the best possible resolution is obtained by the method as described in claim 5.

If however the frequencies which can be reached with the equipment (pulsators) available are not relatively high, or if such high measuring frequencies are not suitable for proper control of the measurement process, then the method of measurement described in claim 6 should be employed.

Particularly good reoslution can then be achieved, if the method is carried out in accordance with claim 7.

If the method is carried out according to claim 8 or claim 9, it is not necessary to relate the registered change in frequency characteristic with the momentarily prevailing loading conditions.

The method of measurement according to claim 10 is called for when, for reasons of safety, measurements must not be taken in certain frequency ranges or in contrary, to optimize efficiency, when measurements should in fact be taken at particular parts of the frequency-characteristic curve, independent of crack propagation. The procedure according to claim 11 provides for optimization of efficiency.

Since there are pulsators on the market which, for reasons of optimizing efficiency, are operated continuously in resonance, the proposed method of measurement should be carried out in accordance with claims 12 or 13, depending on whether internal control of the pulsator is available or not.

A high frequency pulsator for carrying out the method of the invention is described in claim 14.

To reach highest frequencies, a high frequency pulsator as described by the wording of claim 15 is required; the version described in claim 16 provides an ideal force-drive or movement-drive.

The invention will now be described by way of example and with the help of diagrams viz., FIG. 1: The qualitative frequency response curve (Bode diagram) produced by a sample.

FIG. 1a: The amplitude-frequency characteristic of the quotients of sample movement $\bar{v}$ and applied loading force $\bar{F}$, in the following generally denoted as the mechanical impedance $\bar{Z}$.

FIG. 1b: The phase-frequency characteristic of the above mentioned mechanical impedance.

FIG. 2: A block diagram of a measuring process for evaluating crack induced changes in the amplitude frequency characteristic of a mechanical impedance at constant, controlled force drive or speed drive.

FIG. 3: A block diagram of a measuring process for evaluating crack induced changes in the phase frequency characteristic of a mechanical impedance.

FIG. 4: A block diagram of a measuring process for automatically adapting a measuring frequency to provide for a controlled constant phasing of a mechanical impedance, latter changing with crack propagation.

Figure 5:
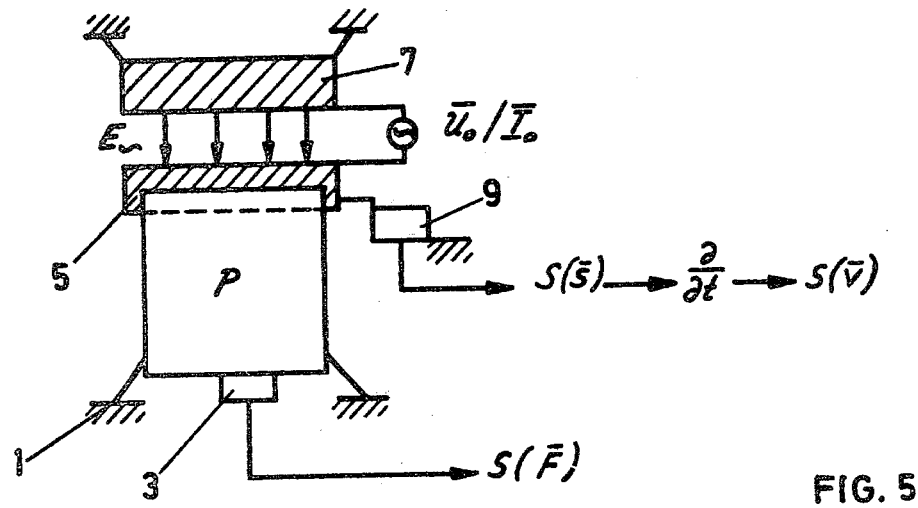

FIG. 5: The basic arrangement of a high frequency pulsator with direct, electromagnetic transmission of the load.

Figure 6:
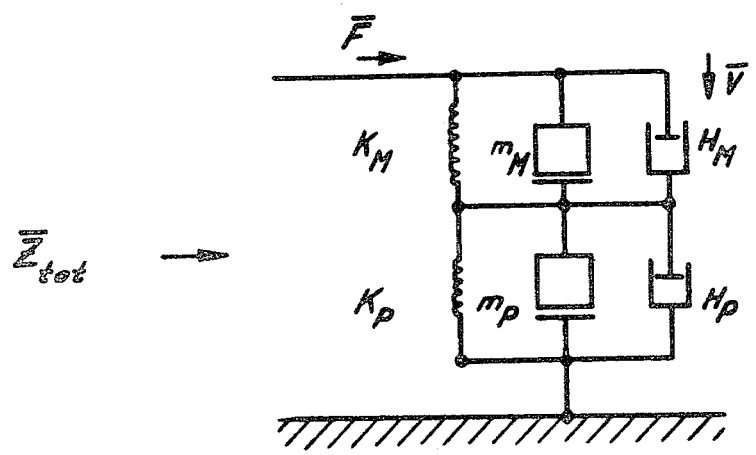

FIG. 6: A mechanical equivalent-circuit diagram for the coupling of the sample and the pulsator mass.

Figure 7:
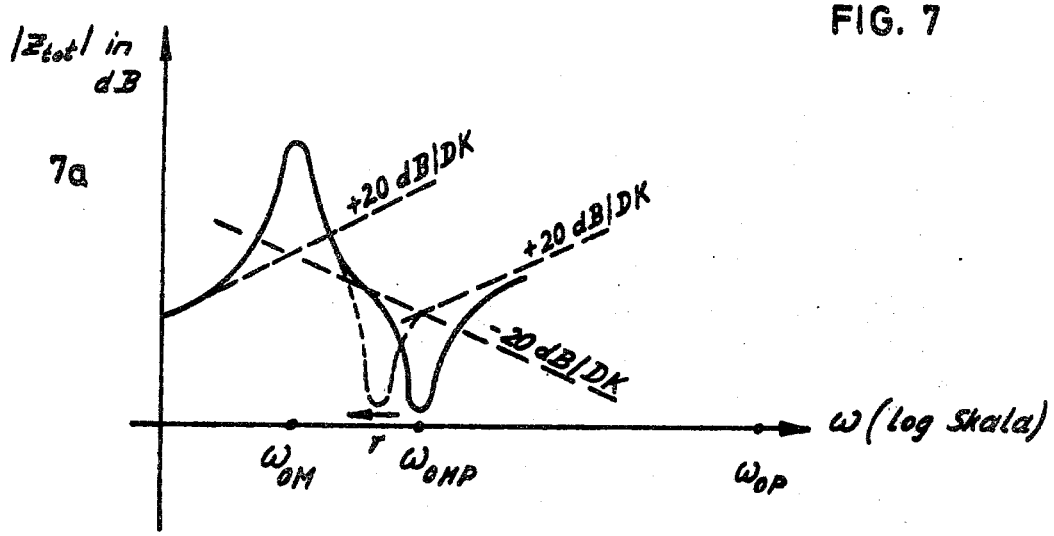

FIG. 7: A qualitative representation of the frequency response characteristic of the equivalent circuit diagram shown in FIG. 6 (Bode diagram).

FIG. 7a: The amplitude-frequency characteristic and,

FIG. 7b: the phase-frequency characteristic.

Figure 8:
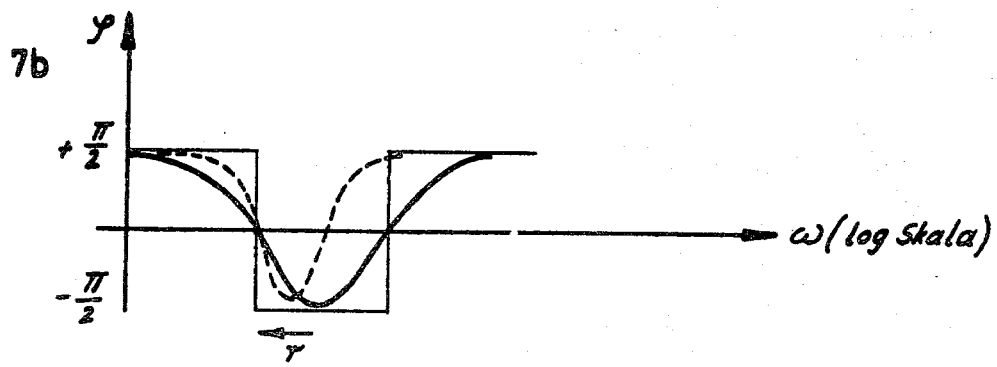
Figure 8:
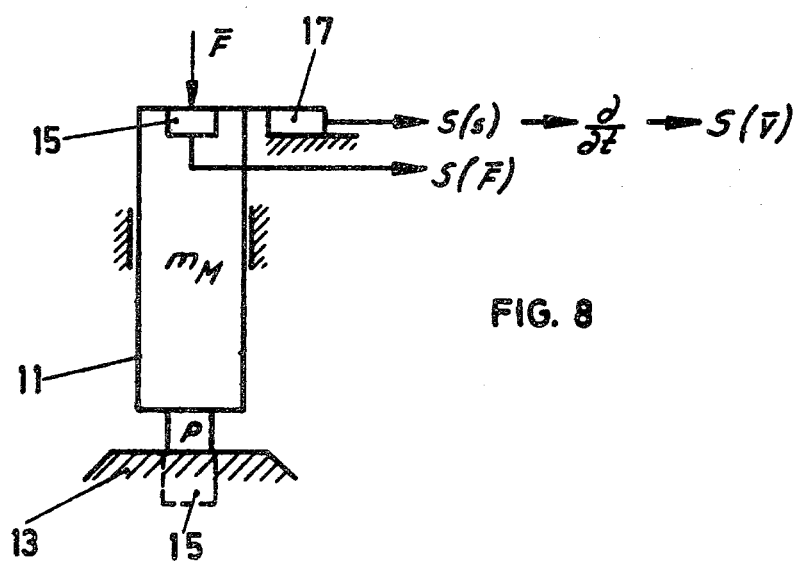

FIG. 8: A basic arrangement of a mechanical pulsator with devices for measuring force and movement.

Figure 9:
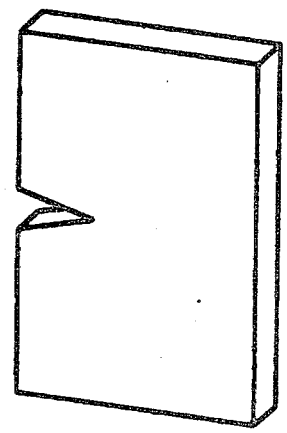

FIG. 9: A notched specimen or probe as is known as fracture mechanic specimen and which provides a required well defined crack, namely the notch.

Throughout the description the expressions sample, specimen or probe are used for the material piece to be tested.

The frequency response of a sample P can be illustrated, for example, via its mechanical impedance (partial impedance with subscript P in FIG. 6), which can be defined as the quotient of the relative velocity $\bar{v}$ of its ends and the force $\bar{F}$ acting on the sample. As such $\bar{v}$ and $\bar{F}$ are complex quantities.

The impedance $\bar{Z}(p) = \bar{Z}(j\omega)$ of the sample is:

$$\bar{Z}_p(p) = \frac{p(1/K_P)}{1 + p \cdot \frac{2\xi_P}{\omega_{oP}} + p^2 \cdot \frac{1}{\omega_{oP}^2}} \quad (1)$$

where
$K_P$ = the elastic constant of the sample
$\xi_P$ = the attenuation constant of the sample
$\quad = H_P(m_P \cdot K_P)^{-\frac{1}{2}}$ (2)
$H_p$ = friction which is linearly dependent on the velocity
$m_p$ = mass of the sample $$\omega_{oP} = \text{basic resonance frequency of the sample} = \sqrt{\frac{K_p}{m_p}} \quad (3)$$

FIG. 1 shows qualitatively, in the form of a Bode diagram, the frequency response of the impedance $\bar{Z}_P(p)$ of the sample. The Bode Diagram comprises an amplitude versus frequency-plot both axes being logarithmically scaled (amplitude e.g. in dB = 20 log/z/), which plot is related to as amplitude-plot as well as a phase versus frequency plot, where only the frequency axis logarithmically scaled, denoted as phase-plot. At a pulsation frequency $\omega = \omega_{oP}$ there is a resonance rise or peak in the amplitude frequency characteristic (FIG. 1a) which is the larger, the smaller the value $\xi_P$ is. On both sides of the resonant frequency $\omega_{oP}$ the amplitude decreases asymtotically towards $-20$ dB per frequency decade.

The elastic constant $K_P$ of the sample is:

$$K_P = A_P / l_P E_P \quad (4)$$

where:
$A_P$ = the cross-sectional area of the sample, perpendicular to the pulsating force acting on the sample
$l_P$ = the length of sample in the direction of the applied force
$E_P$ = the elastic modulus of the sample material When a crack grows in the sample, the cross-sectional area $A_P$ which appears in the expression for the constant $K_P$ is reduced. It is easy to check that the relative change in the resonant frequency $d\omega_{oP}/\omega_{oP}$ is equal to the relative change $dA_P/A_P$, i.e. the resonant frequency of the sample shifts, relative to its value at smaller crack extent, to the same extent towards lower frequencies as the cross-sectional area $A_P$ decreases relative to its value at said smaller crack extent, due to the growth of the transverse crack. As can be seen from equation (2) $\xi_P$ increases together with a decrease in the resonant frequency due to the decrease in cross-sectional area $A_P$ which affects the elastic constant $K_P$. From this, it can be seen that in the case of progressive crack growth, and the consequent reduction in the resonant frequency $\omega_{oP}$, there is also a decrease in the resonance peak. This is indicated in FIG. 1 by broken lines and by the arrows S.

FIG. 1b shows the phase-frequency characteristic of the impedance $\bar{Z}_P(p)$. From this, it becomes clear that for small frequencies the phase $\phi$ approaches the value $+\pi/2$, at the resonant frequency $\omega_{oP}$ being equal to zero, and for large frequencies approaching $-\pi/2$. As in FIG. 1a for the amplitude-frequency response, in FIG. 1b the qualitative change in the phase-frequency response for progressive crack growth is shown in broken lines. These changes in frequency response of the mechanical impedance $\bar{Z}_P(p)$ of the sample under the test can now be utilised to measure the growth of the crack. FIGS. 2–4 show the block diagrams for the measuring process. In the method of measurement shown in FIG. 2, a pulsating force $\bar{F}$ or a speed of pulsation $\bar{v}$ is applied to the sample via a drive M.

As such, the drive is preferably controlled so that:

$$|\bar{F}| = \text{constant} = F_o \quad (a)$$

or $$|\bar{v}| = \text{constant} = \bar{v}_o \quad (b)$$

$(|x| = \text{Amplitude of } x)$

In general, these two possibilities are also shown in FIGS. 3 and 4 by the symbols $\bar{F}$ or $\bar{v}$ each on the appropriate side of the signal path, as alternative possibilities.

In case (a)

$$G(p) = \bar{Z}_p(p)$$

i.e. for a constant applied pulsating force, the sample with propagating crack $A_P(N)$ (N = number of load cycles) produces a change in the speed of pulsation as follows:

$$|\bar{v}| = F_o \cdot |\bar{Z}_P(p)|$$

For equation (b) above the following holds:

$$G(p) = \bar{Z}_p(p)^{-1} \text{ and therefore}$$
$$/\bar{F}/ = /\bar{Z}_p(p)^{-1}/ \cdot v_o$$

The impedance $\bar{Z}_P(p)$ of the sample is influenced by the crack propagation, which depends on the number of loads cycles (N), and therefore by the accompanying change in cross-sectional area $A_P(N)$. The magnitude of the variable parameter $\bar{v}$ or $\bar{F}$ i.e. $|\bar{v}|$ or $|\bar{F}|$ is taken as the measuring criterion. In this measuring process the frequency is constantly maintained at a measuring frequency $\omega_m$. As can be seen from FIGS. 1a and 1b this measuring frequency $\omega_m$ is preferably chosen to be greater than the resonant frequency $\omega_{oPo}$ of the sample at initial crack, so that with decreasing resonant frequency $\omega_{op}$ in the sample, the largest possible change $\Delta|Z|$ impedance value $|\bar{Z}_p(p)|$ is obtained.

In the method according to the block diagram in FIG. 3 a drive M is employed. Here the drive does not have to be controlled. The pulsating force $\bar{F}$ and the movement or speed of $\bar{v}$ of the pulsation are measured. For measuring the force piezo force measuring equipment as from Fa. "Kistler Instrumente AG" Switzerland may be used, for speed measurement eg. acceleration transducer as from Fa. "PYE DYNAMICS LTD" England or from Fa. "Mesotron AG" Switzerland.

The following relationship holds $$\bar{F} = \bar{Z}_p(p)^{-1} \cdot \bar{v}; \ \bar{Z}_p(p)^{-1} = \}\ \bar{F} - \}\ \bar{v}$$

or $$\bar{v} = \bar{Z}_p(p)\bar{F}; \quad \bar{Z}_p(p) = \}; \quad \bar{v} - \} \bar{F}$$

Instead of evaluating a change in the amplitude frequency characteristic of the impedance-frequency response, the change in the phase-frequency characteristic is detected for the measurement of crack propagation corresponding to the area $A_p(N)$ which changes with N i.e. with time. For this, the force $\bar{F}$ applied to the sample and the resultant, velocity $\bar{V}$ detected are brought together in a phase-measurement unit $\Delta \phi$. Phase measurement units are well-known in electronic technique. The phase difference between the force $\bar{F}$ acting on the sample and the velocity $\bar{v}$ corresponds to the impedance-phase, as in FIG. 1b, which changes as shown by arrow S with propagation of the crack.

The detection of the velocity at the non-stationary end of the sample attached to the pulsator can be achieved by conventional means e.g. by opto-electrical means or using a piezo-element, or by detecting the distance moved e.g. with inductive distance measuring equipments as from Fa. "Mesotron", and relating it to the time required e.g. by differentiation. Also devices for measuring a pulsating force as $\bar{F}$, for example pressure gauges are known as was stated above. The signals $\bar{v}$ and $\bar{F}$ to be detected are preferably converted into electrical signals directly by the detectors, or by subsequent means. As velocity and force signals are convertable into electrical signals, the resultant determination of the magnitude can be carried out without problem by the method shown in FIGS. 2 and 3, likewise the subsequent combination of the signals for phase detection.

FIG. 4 shows the block diagram for a method with shifting the measuring frequency, so that the change in resonant frequency of the sample $\omega_{oP}$ ($\Delta\omega_{op}$ in FIG. 1a) is measured. In principle this method of measurement can be realised by controlling the measuring frequency on the resonant peak of the amplitude-frequency characteristic. This method however requires a lot of effort, as the peak value alters as a function of the resonant frequency as was shown above. The evaluation of the phase-frequency characteristic is much better suited for controlling the frequency shift. The singularity of the zero crossing of the phase plot of the varying resonant frequency $\omega_{op}$ can be usefully employed for this purpose. For this reason the method illustrated by FIG. 4 is based on that shown in FIG. 3, but with the difference that the phase difference $\Delta \varphi$ which is detected is compared with a given value $\Delta \varphi_o$ as a reference value e.g. $\Delta\omega_o = o$, and the resultant difference $S(\Delta \varphi_o - \Delta \varphi)$, converted to a frequency control signal S ($\Delta \omega$), which is fed back to the drive M to control the frequency. The measuring frequency is shifted until $(\Delta \varphi_o - \Delta \varphi) = o$ where latter frequency matches the momentary resonant frequency. This method of measurement thus uses a phase locked loop. The measuring frequency which follows the resonant frequency is evaluated as the measuring signal.

The direct measurement of the sample frequency response, as was explained with the help of FIGS. 1–4, sets very high demands on the construction of the pulsator. This becomes apparent immediately when one considers that for example an aluminium sample with an elastic modulus of $$E_p = 7.2 \cdot 10^9 \cdot 9.81 \cdot N_2/m$$

a cross-sectional area $$A_p(o) = 0.001 \ m^2$$

and a sample length $$l_p = 0.1 \ m$$

has a resonant frequency of ca. 16 kHz.

If the frequency response of the sample is not to be disturbed by the pulsator itself, then all resonant frequencies occurring on the pulsator must be much higher than the resonant frequency $\omega_{op}$ of the sample. This means that only an extremely small mass may pulsate on the pulsator, which in practice means that the transfer of load from the pulsator to the sample cannot be performed mechanically by mechanical contact, but for example electro-magnetically by means of electrical fields providing a force on the sample. Furthermore, since the measurement frequency is preferably chosen to be above the resonant frequency $\omega_{op}$ of the sample, when the amplitude-frequency characteristic is exploited, the process as outlined by FIG. 2 results in such a large number of loading cycles in such a short time, that considerable effort is required to obtain a suitable, very rapid measurement system to evaluate the measurement signals and which also allows for changing the load on reaching certain crack lengths or previously specified numbers of load cycles. On exploiting the change in phase-frequency characteristic of the sample impedance, measurement frequencies which lie below the resonant frequency of the sample can as well be employed. For good detection of the phase changes, however, the measurement frequency should lie approximately within the resonance band-width. This is given by the two frequency-values at which the amplitude-frequency characteristic, relative to its resonant peak, has fallen to $1/\sqrt{2}$ of its value. Here too one has to reckon with very large numbers of load cycles per unit time. To carry out the process described up to now one could hardly use the conventional pulsators with their pulsating masses.

FIG. 5 shows schematically the construction of an electromagnetic pulsator, with the help of which, because of its small additional inertia, one can achieve measurement frequencies which are larger than the resonant frequency of the sample. The sample P is held on one side in a holder 1. A device for measuring the applied force, for example a load cell 3, as piezo force measuring equipments from Fa. "Kistler" registers the force applied to the sample via the holder 1 and gives a signal $S(\bar{F})$ which is proportional to the applied force $\bar{F}$. The load cell 3 is preferably in the form of a mechanical/electrical converter and provides therefore an electrical output signal. The sample P is, at its non-clamped end, provided with a cap 5 of highly magnetic material which however, compared with the sample, is of almost negligible mass. Directly opposite the cap 5 there is a stationary magnetic counter pole 7 of magnetic conductive material and, between pole 7 and cap 5, there is an electric generator which is controlled (not shown) to maintain constant output voltage amplitude $\bar{U}_o$ or constant output current amplitude $\bar{I}_o$ is required, and thus works as an ideal drive for speed or force respectively. The driving force is applied to the cap 5 and therefore to the sample via the applied alternating field $E \sim$ in the air gap between pole 7 and cap 5. The velocity of the non-clamped end of the sample can for example be registered by means of a piezo-element e.g. again from Fa. "Kistler", which delivers an electric signal S(s̄) as a function of its elongation. The differentiation of this signal as a function of time yields an electrical signal as a measure of the velocity $\bar{v}$ of the sample P. Maintaining the generator voltage $\bar{U}_o$ constant is analogous to maintaining the sample velocity $\bar{v}$ constant, whilst maintaining the generator current $\bar{I}_o$ current corresponds to the realisation of a drive for constant force, as in FIG. 2.

A conventional pulsator with relatively large pulsating mass on the drive leads to a equivalent circuit-diagram shown in FIG. 6, where:

$K_M$ is the elastic constant of the pulsating mass on the pulsator $m_M$ is the pulsating mass of the pulsator $H_M$ is the friction which is dependent on the speed and acts on the pulsator mass during pulsation $K_p$ is the elastic constant of the sample $m_p$ is the mass of the sample $H_p$ is the velocity dependent friction on the sample The driving means encounter thus, as a first approximation, a mechanical impedance $\bar{Z}_{tot}(p)$ of $$\bar{Z}_{tot}(p) = \frac{p\left(1 + \frac{2\xi_{MP}}{\omega_{oMP}}p + \left(\frac{p}{\omega_{oMP}}\right)^2\right)}{\left(1 + p\frac{2\xi_p}{\omega_{oP}} + \left(\frac{p}{\omega_{oP}}\right)^2\right)\left(1 + p\frac{2\xi_M}{\omega_{oM}} + \left(\frac{p}{\omega_{oM}}\right)^2\right)} \quad (5)$$

where: $\omega_{oMP}$ is the series resonant frequency of the equivalent circuit diagram as shown in FIG. 6, and where:

$$\omega_{oMP} = \left(\frac{K_M + K_P}{m_M + m_P}\right)^{\frac{1}{2}} \quad (6)$$

$\xi_{MP}$ is the damping constant of the whole circuit, and where:

$$2\xi_{MP} = (H_M + H_p) \cdot (m_M + m_p)^{-\frac{1}{2}} \cdot (K_M + K_p)^{-\frac{1}{2}} \quad (7)$$

and: $\omega_{op}$ is a parallel resonant frequency of the equivalent circuit diagram, as shown in FIG. 6, during resonance of the sample, where equation (3) holds. Equation (2) is valid also.

$\omega_{oM}$ is a parallel resonant frequency of the equivalent circuit diagram in FIG. 6 during resonance of the pulsator mass, whereby the following holds:

$$\omega_{oM} = \left(\frac{K_M}{m_M}\right)^{\frac{1}{2}} \quad (8)$$

and for the corresponding damping constant:

$$\xi_M = H_M(m_M \cdot K_M)^{-\frac{1}{2}}$$

From the above it is clear that the resonant frequency $\omega_{oM}$ is not dependent on the elastic constant $K_p$ of the sample, and is therefore independent of crack propagation. Only the parallel resonance $\omega_{oP}$ of the sample and the series resonance of the overall set up $\omega_{oMP}$ depends on the crack propagation.

For the conventional magnitudes of modulus of elasticity and pulsator masses the following holds:

$$\omega_{oM} < \omega_{oMP} < < \omega_{oP} \quad (10)$$

The Bode diagram of the frequency response of the mechanical impedance $\bar{Z}_{tot}(p)$ can thus be deducted to be as shown in FIGS. 7a, b.

The resultant frequencies $\omega_{oM}$ and $\omega_{oMP}$ are, for a steel pulsator mass and aluminium sample:

$\omega_{oM} \cong 540$ Hz $\omega_{oMP} \cong 630$ Hz for the following pulsator and sample specifications:

| | |
|---|---|
| Length of the sample | : 0.1 m |
| Breadth of sample | : 0.05 m |
| Thickness of sample | : 0.02 m |
| Modulus of elasticity of aluminium $E_{Al}$ | : $7.2 \cdot 10^9 \cdot 9.81 \frac{N}{m^2}$ |
| Specific mass of aluminium $\rho_{Al}$ | : $2.7 \cdot 9.81 \cdot 10^3 \frac{kg}{m^3}$ |
| Cross-sectional area of the pulsator mass | : $0.1^2 \cdot \pi m^2$ |
| Length of the pulsator mass: | 3 m |
| Modulus of elasticity of steel | : $21 \cdot 10^9 \cdot 9.81 \frac{N}{m^2}$ |
| Specific mass of steel | : $\rho_{Fe} = 7.9 \cdot 9.81 \cdot 10^3 \frac{kg}{m^3}$ |

Furthermore, with optimum lubrication of the pulsator mass relatively small values for $\xi_{MP}$ and certainly for $\xi_P$ are obtained, so that pronounced peaks occur in resonance at $\omega_{oM}$ and $\omega_{oMP}$. Keeping this in mind, together with the fact that $\omega_{oM}$ and $\omega_{oMP}$ lie relatively close together, it is then apparent that the amplitudefrequency characteristic of the impedance $\bar{Z}_{tot}(p)$ runs relatively steeply between these frequencies mentioned above and can be steeper than −20 dB per frequency decade. In this range the amplitude-frequency characteristic represents a good discrimination characteristic. With advancing crack propagation the elastic constant of the sample $K_P$ decreases, thus producing a shift in the resonant frequency $\omega_{oMP}$ towards smaller frequencies, as indicated by the arrow r and the broken line in FIG. 7. Since the resonant frequency $\omega_{oM}$ remains unchanged during crack propagation, an increasingly better line of discrimination would be obtained, if the corresponding resonance-peak were not reduced with decreasing resonant frequency $\omega_{oMP}$. Since, however, the resonant frequency $\omega_{oM}$ and likewise $\xi_M$ remain constant, independent of crack propagation, the resonance behaviour of the pulsator ensures an adequately steep discrimination-characteristic $$\frac{\partial/\bar{Z}_{tot}(p)/}{\partial \omega_{oMP}}$$

even on samples which are practically broken through.

With the above mentioned numerical values, the percentage change in resonant frequency $\omega_{oMP}$ obtained is about 8 times smaller than the percentage change in the cross-sectional area of the speciment, which decreases as the crack propagates and which affects the elastic constants. This was confirmed experimentally in that factors of 4–12 times were measured, depending on the sample used. The tests performed were done with the at the moment preferred method of keeping the pulsating system in resonance.

It follows that, with a choice of resonant frequencies according to the equation (10), good discrimination of crack propagation can be achieved if use is made of the evaluation of the amplitude-frequency characteristic, or by evaluation of the phase-frequency characteristic. When setting the selected pulsator with respect ot a given sample, according to equation (10), the following equation must be observed:

$$K_P/K_M > m_P/m_M$$

The frequency of pulsating (measuring frequency) is preferably chosen according to $$\omega_{oM} < \omega < \omega_{oMP} \quad (11)$$

which means that the steep part of the amplitude-frequency curve between $\omega_{oM}$ and $\omega_{oMP}$ is exploited, or else $$\omega \gtreqless \omega_{oMP}$$

The measuring process itself can again be carried out as in the diagrams shown in FIGS. 2–4.

FIG. 8 shows the basic construction of the measuring arrangement using a conventional pulsator. The pulsating mass 11 of the pulsator of mass $m_M$, connected in series to the sample P, is set into pulsating movement with the force $\bar{F}$ by means of a drive mechanism which is not shown here. The sample P is clamped between the lower end of the pulsator mass and the stationary machine block 13. The force $\bar{F}$ is detected by a force measurement device as were mentioned above, for example a load cell 15, which gives off a signal $S(\bar{F})$. From FIG. 6 it is clear that the force measurement equipment, for example the load cell 15, can be arranged at any suitable place. As indicated here by broken lines, this can also be on the machine block 13. The speed of the pulsator mass 11 is, as shown in FIG. 8, detected at that end of the mass apart from the sample P, using for example a piezo electric element 17 as was also mentioned above. Depending on the measuring principle employed, the signal $S(\bar{F})$ can be used to control for constant applied force $|\bar{F}|$ as a feedback signal to the drive (not shown) or, to control for constant pulsating speed $|\bar{v}|$, the signal $S(\bar{v})$ can be fed back.

At this point the direct analogy of two serially connected electrical parallel resonance circuits and the mechanical equivalent circuit of FIG. 6 is mentioned to be considered, whereby $\bar{F}$ is directly analogous to current $\bar{I}$ and velocity $\bar{v}$ to voltage $\bar{U}$.

It is also known that there are on the market mechanical pulsators which are always operated in resonance in order to optimise their efficiency i.e. they have frequency control as shown in FIG. 4, however for a completely different purpose, i.e. to reduce power requirement and not to provide the frequency as signal to quantitatively follow crack propagation. It is evident, however, that these pulsators are extremely suitable for carrying out the measurement technique proposed here without requiring much change in construction; only the frequency plot of $\bar{F}$ or $\bar{v}$ has to be registered. The detection of frequency represents no technical problem whatever and can for example be realized by counting the number of zero crossings per time unit. Of course, frequency control can also be carried out at other points than at resonant frequency; because of the smaller slope however, for example in the frequency/phase plot, large instabilities can occur.

If, on measuring the amplitude-frequency characteristic, no control means is provided to hold the applied force amplitude or speed amplitude constant, then the proposed method of measurement can still be used; the measurement signal $|\bar{v}|$ or $|\bar{F}|$ then has to be calibrated by the appropriate momentarily driving values $|\bar{F}|$ or $|\bar{v}|$ respectively.

The proposed method of measurement can, without problem, be carried out automatically using a programmable (for example computer controlled) pulsator, as a result of which extremely efficient utilisation of the test facility can be achieved during daytime and night-time. There is also the possibility of controlling the test according to the number of load cycles N or the length of crack a(N), and for example of interrupting or terminating the test after a given number of load cycles $N_o$ or at a given crack length $a_o$. A big advantage of the proposed method of measurement is that the change in cross-sectiona area due to crack propagation in the sample is measured; this change directly affects the elastic constant $K_P$ of the sample. Consequently the projection of all cracks i.e. also secondary cracks on the plane normal to the direction of pulsation is sensed. This is not possible by the conventional method of optical inspection of the crack at the surface. When using conventional mechanical pulsators, only small extra expenditure is required to allow the proposed method of measurement to be used with these pulsators.

In FIG. 9 a sample or probe, known as fracture mechanic specimen with a notch is shown. The notch is the initial crack, the propagation of which is to be measured. When using probes without initial crack uncertainity is encountered about when a crack occurs.

The described method is not only applicable on fracture mechanic probes but on all probes which are pre-cracked, whereby the initial crack may have been detected by other known method, e.g., by observation of the probe surface.

As examples, the following commercially available device as referred to within the description are listed:

|  | from: |
|---|---|
| Acceleration transducer UA1 | Pye Dynamics Ltd., GB-Watford |
| Frequency-counter | Dana Laboratories USA-California |
| Force registering units | Rumul CH-Schaffhuasen |
| Force and acceleration measuring units (piezo) | Kistler Instrumente CH-Winterthur |
| Electro-magnetic resonance machines | Instron Ltd., GB-High Wycombe Bucks |
| Induction way-measuring units | Mesotron AG CH-Killwangen |

What is claimed is:

1. Method of measuring crack propagation in sample of materials under alternating stress which comprises applying alternating load to a pre-cracked specimen or probe of material registering the mechanical impedance ($\bar{Z}_P(p)$; $\bar{Z}_{tot}(p)$) of the specimen, which is due to the propagation of the crack and which is defined as a vector quotient of velocity ($\bar{v}$) and force ($\bar{F}$) in the complex plane, and registering the change in frequency response or behavior of said impedance as a measure of crack propagation.

2. Method of measurement according to claim 1, in which a change in the amplitude-frequency characteristic ($|\bar{Z}_p(p)|$) is registered.

3. Method of measurement according to claim 1, in which a change in the phase-frequency characteristic ($\sphericalangle\bar{Z}_P(p)$; $\sphericalangle\bar{Z}_{tot}(p)$) is registered.

4. Method of measurement according to claim 1, in which registration is made of the change in frequency response in the frequency range of a resonance frequency ($\omega_{oP}$, $\omega_{oPM}$) of a mechanical impedance ($\bar{Z}_P(p)$; $\bar{Z}_{tot}(p)$) influenced by the propagation of the crack.

5. Method of measurement according to claim 1, in which at least one change in the frequency response of the mechanical impedance ($\bar{Z}_P(p)$) of the sample is registered in that the ratio of the sample displacement to the applied force is registered as a measure of the propagation of the crack.

6. Method of measurement according to claim 1, in which, with respect to the alternating stress applied to the sample (P), at least one load ($m_M$) is provided in series, the impedance ($\bar{Z}_M(p)$) of which has a resonant frequency ($\omega_{oM}$) smaller than the resonant frequency of the sample ($\omega_{oP}$), corresponding to the fundamental harmonic frequency, and that changes in the frequency response in the frequency range of a resonant frequency ($\omega_{oMP}$) are registered, where load ($m_M$) and sample (P) are both in resonance.

7. Method of measurement according to claim 6, in which changes in frequency response in the frequency range of the resonant frequency ($\omega_{oPM}$) in question are registered, and which corresponds to the fundamental harmonic frequency at which load and sample are in resonance.

8. Method of measurement according to claim 1, in which a load amplitude ($\bar{F}$) is kept constant ($F_o$), for example by means of a drive (M) controlled for this condition, and a movement amplitude ($|\bar{v}|$) is registered.

9. Method of measurement according to claim 1, in which a movement amplitude ($|\bar{v}|$) is kept constant ($v_o$), for example by means of a drive (M) controlled by this condition, and a load amplitude ($|\bar{F}|$) is registered.

10. Method of measurement according to claim 1, in which the stress frequency ($\omega$) is controlled for a given amplitude ($|\bar{F}|$; $|\bar{v}|$) and/or phase criterion ($\phi$) of the frequency response and the stress frequency ($\omega$) is recorded.

11. Method of measurement according to claims 5 or 10, in which the stress frequency ($\omega$) is controlled on a resonant frequency ($\omega_{oP}$, $\omega_{oPM}$).

12. Method of measurement according to claim 11, in which the control is made by means of an amplitude—($|\bar{F}|$; $|\bar{v}|$) extreme value detection.

13. Method of measurement according to claim 11, in which the control is made by means of a phase locked loop.

14. High frequency pulsator for carrying out the process according to claim 1, comprising transmission means (1,5,7; 11,13) transmitting the stress to the sample (P); first measuring means (9; 17) to measure the movement ($\bar{v}$) due to the alternating stress, for example in the form of a piezo electric crystal; second measuring means (3,15) to measure the applied force ($\bar{F}$).

15. High frequency pulsator according to claim 14, in which the transmission means comprises a first pole (5) securely mounted at one end of the sample, and a second, stationary pole (7) separated from the first by an air gap, both being made of electrically conductive materials, comprising an electrical oscillator connected between the poles (5,7) in order to apply a stress to the sample by means of the field (E) produced in the air gap, the mass of the first pole (5) being negligeably small compared with that of the sample.

16. High frequency pulsator according to claim 15, in which the oscillator acts as constant voltage-amplitude source or constant current-amplitude source, being therefore controlled by means of a feedback loop.

* * * * *

UNITED STATES PATENT AND TRADEMARK OFFICE
CERTIFICATE OF CORRECTION

PATENT NO. : 4,307,610

DATED : December 29, 1981

INVENTOR(S) : Jürg Leupp

It is certified that error appears in the above-identified patent and that said Letters Patent are hereby corrected as shown below:

Column 1, line 12, change "(crank" to ---(crack---.

Column 1, line 21, change "from" to ---when---.

Column 2, lines 44-45, change "amplitude frequency" to ---amplitude-frequency---.

Column 3, line 33, after "axis" insert ---is---.

Column 5, line 12, change "$\overline{V}$" to ---$\overline{v}$---.

Column 5, line 46, change "of", second occurrence, to -- at --.

Column 5, line 52, change "$\Delta\omega_o = o$" to ---$\Delta f_o = o$---.

Column 7, line 9, change "current", second occurrence, to ---constant---.

Column 8, line 7, change "deducted" to ---deduced---.

Column 8, line 9, change "resultant" to ---resonant---.

Column 8, lines 42-43, change "amplitudefrequency" to ---amplitude-frequency---.

Column 9, line 2, change "speciment" to ---specimen---.

UNITED STATES PATENT AND TRADEMARK OFFICE
CERTIFICATE OF CORRECTION

PATENT NO. : 4,307,610

DATED : December 29, 1981

INVENTOR(S) : Jürg Leupp

It is certified that error appears in the above-identified patent and that said Letters Patent are hereby corrected as shown below:

Column 9, line 20, change "pulsating" to ---pulsation---.

Column 10, line 28, change "cross-sectiona" to ---cross-section---.

Column 10, line 49, change "device" to ---devices---.

Column 10, line 65, claim 1, change "sample" to ---samples---.

Column 10, line 67, claim 1, after "applying" insert ---an---.

Column 10, line 68, claim 1, after "material" insert ---,---.

Signed and Sealed this

Thirtieth Day of March 1982

[SEAL]

Attest:

Attesting Officer

GERALD J. MOSSINGHOFF

*Commissioner of Patents and Trademarks*